United States Patent

Yamazaki

(10) Patent No.: US 9,682,913 B2
(45) Date of Patent: Jun. 20, 2017

(54) METHOD FOR IMPROVING OPTICAL PURITY OF 2-HYDROXYCARBOXYLIC ACID OR DERIVATIVE THEREOF

(71) Applicant: KOWA COMPANY, LTD., Nagoya-shi, Aichi (JP)

(72) Inventor: Yukiyoshi Yamazaki, Tokyo (JP)

(73) Assignee: KOWA COMPANY, LTD., Aichi (JP)

( * ) Notice: Subject to any disclaimer, the term of this patent is extended or adjusted under 35 U.S.C. 154(b) by 0 days.

(21) Appl. No.: 14/780,625

(22) PCT Filed: Mar. 28, 2014

(86) PCT No.: PCT/JP2014/059083
§ 371 (c)(1),
(2) Date: Sep. 28, 2015

(87) PCT Pub. No.: WO2014/157607
PCT Pub. Date: Oct. 2, 2014

(65) Prior Publication Data
US 2016/0060203 A1  Mar. 3, 2016

(30) Foreign Application Priority Data

Mar. 29, 2013 (JP) ................. 2013-075396

(51) Int. Cl.
C07B 57/00 (2006.01)
C07C 51/41 (2006.01)
A61K 31/423 (2006.01)
C07D 263/58 (2006.01)
C07C 67/08 (2006.01)

(52) U.S. Cl.
CPC .......... *C07C 51/412* (2013.01); *A61K 31/423* (2013.01); *C07B 57/00* (2013.01); *C07C 67/08* (2013.01); *C07D 263/58* (2013.01)

(58) Field of Classification Search
CPC .............................. C07C 51/412; C07B 57/00
See application file for complete search history.

(56) References Cited

U.S. PATENT DOCUMENTS

| 7,094,926 B2 * | 8/2006 | Amano | .................. C07C 51/04 562/602 |
|---|---|---|---|
| 2005/0101636 A1 | 5/2005 | Yamazaki et al. | |
| 2005/0245764 A1 | 11/2005 | Yamashita et al. | |

(Continued)

FOREIGN PATENT DOCUMENTS

EP 1852426 A1 11/2007
EP 1908747 A 4/2008
(Continued)

OTHER PUBLICATIONS

Extended European Search Report pursuant to Rule 62 EPC, the supplementary European Search Report and Search Opinion, mailed Aug. 10, 2016; for Application No. 14772858.8-1454/2980061 (8 pgs.).
Corrected European Search Report pursuant to Rule 62 EPC, the supplementary European Search Report and Search Opinion, mailed Sep. 26, 2016; for Application No. 14772858.8-1454/2980061 (4pgs.).
K. Nakamura et al., "Stereochemical Control on Yeast Reduction of a-Keto Esters. Reduction Immobilized Bakers' Yeast Hexane", J. Org. Chem., vol. 53, pp. 2589-2593 (1988).

(Continued)

*Primary Examiner* — Golam M M Shameem
(74) *Attorney, Agent, or Firm* — Finnegan, Henderson, Farabow, Garrett & Dunner, LLP

(57) ABSTRACT

To provide a method for improving optical purity of an optically active 2-hydroxycarboxylic acid or a derivative thereof, which is useful as a raw material in the manufacture of medicines, agrochemicais, and industrial products. The method of the invention for improving purity of a hydroxycarboxylic acid of the following formula (1a) or (1b) or a derivative thereof includes the steps of reacting the hydroxycarboxylic acid of the following formula (1a) or (1b) with at least one optically inactive base selected from the group consisting of an alkali metal, alkoxide and a secondary amine in the presence of a solvent and, subsequently, performing recrystallization, to thereby form a hydroxycarboxylic acid salt of the following formula (IIIa) or (IIIb):

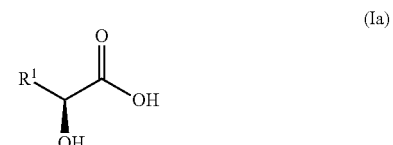

(Ia)

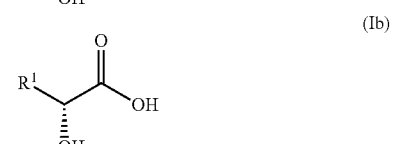

(Ib)

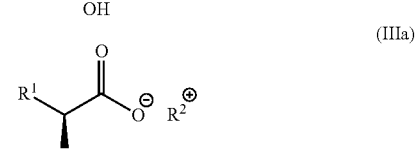

(IIIa)

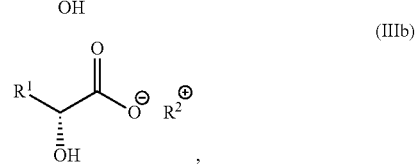

(IIIb)

wherein $R^1$ represents a $C_{1-8}$ alkyl group, and $R^2$ represents an alkali metal or a secondary amine.

9 Claims, No Drawings (Continued)

(56) References Cited

U.S. PATENT DOCUMENTS

| | | |
|---|---|---|
| 2006/0189667 A1 | 8/2006 | Yamazaki et al. |
| 2008/0194833 A1 | 8/2008 | Yamazaki et al. |
| 2009/0023944 A1 | 1/2009 | Yamazaki et al. |
| 2009/0076280 A1 | 3/2009 | Yamazaki et al. |
| 2009/0118535 A1 | 5/2009 | Araki et al. |
| 2009/0209780 A1 | 8/2009 | Koura et al. |

FOREIGN PATENT DOCUMENTS

| | | |
|---|---|---|
| EP | 2457899 A1 | 5/2012 |
| JP | 59-009180 | 1/1984 |
| JP | 1-175956 A | 7/1989 |
| JP | 2000-063321 | 2/2000 |
| JP | 2004-533490 | 11/2004 |
| JP | 2008-044856 A | 2/2008 |
| WO | WO 03/005010 A2 | 1/2003 |
| WO | WO 03/014056 A1 | 2/2003 |
| WO | WO 2005/023777 A1 | 3/2005 |
| WO | WO 2006/090768 A1 | 5/2006 |
| WO | WO 2006/093142 A1 | 9/2006 |
| WO | WO 2006/129649 A1 | 12/2006 |
| WO | WO 2007/013555 A1 | 2/2007 |
| WO | WO 2007/23906 A1 | 3/2007 |

OTHER PUBLICATIONS

R. S. Compagnone et al., "Chirospecific Synthesis of (+)-Pilcarpine", J. Org. Chem., vol. 51, pp. 1713-1719 (1986).

M. Novella Romanelli et al., "Synthesis and Enantioselectivity of the Enantiomers of $PG_8$ and $SM_{21}$, New Potent Analgesic and Cognition-Enhancing Drugs", Chirality, vol. 51, pp. 225-233 (1996).

Mark J. Burk et al, "Rh—DuPHOS-Catalyzed Enantioselective Hydrogenation of Enol Esters. Application to the Synthesis of Highly Enantioenriched a-Hydroxy Esters and 1,2-Diols", J, Am. Chem. Soc., vol. 120, pp. 4315-4353 (1988).

Hakuji Katsura, "Stereochemical Studies on a-Hydroxy Acids (Reports 1 and 2)", Nihon Kagaku Zasshi vol. 77, No. 2, pp. 284-286 (1956).

Atsushi Nakagawa et al., "Asymmetric hydrolusis of 2-hydroxycarboxylic esters using recombinant *Escherochia coli*", Tetrahedron: Asymmetry, vol. 18, pp. 2394-2398 (2007).

D. H. S. Horn et al., "Wool Wax, Part VI. The Synthesis and Stereochemistry of the Straight-chain a-Hydroxy-acids", J. Chem. Soc., vol. 177, pp. 1460-1464 (1954).

Masaaki Nakahata, et al., The Preparation of Optically Pure 3-Hydroxyalkanoic Acid. The Enantioface-differentiating Hydrogenation of the C=O Double Bond with Modified Raney Nickel. XXXVII., Bulletin of the Chemical Society of Japan, vol. 55, No. 7, pp. 2186-2189 (1982).

Tadashi Kikukawa, et al., The preparation of optically pure 3-hydeoxybutanoic acid and its homologues as the dibenzylammonium salt, Chemistry Letters, No. 7, pp. 1267-1270 (1987).

English-language International Search Report from the Japanese Patent Office for International Application No. PCT/JP2014/059083 mailed Jul. 1, 2014.

English-language translation of Written Opinion of the International Search Authority from the Japanese Patent Office for International Application No. PCT/JP2014/059083 mailed Jul. 1, 2014.

\* cited by examiner

METHOD FOR IMPROVING OPTICAL PURITY OF 2-HYDROXYCARBOXYLIC ACID OR DERIVATIVE THEREOF

CROSS REFERENCE TO RELATED APPLICATIONS

This application is a national phase application based on PCT/JP2014/059083, filed Mar. 28, 2014, which claims the priority of Japanese Patent Application Publication No. 2013-075396, filed Mar. 29, 2013, the contents of both of which are incorporated herein by reference.

TECHNICAL FIELD

The present invention relates to a method for improving optical purity of an optically active 2-hydroxycarboxylic acid or a derivative thereof that is useful as a raw material for producing medicines, agrochemicals, and industrial products.

BACKGROUND ART

Optically active 2-hydroxycarboxylic acids are useful compounds as reagents or raw materials in the manufacture of medicines, agrochemicals, and industrial products. For example, 2-hydroxycarboxylic acid can be used as an important raw material of (R)-2-(3-{N-(benzoxazol-2-yl)-N-[3-(4-methoxyphenoxy)propyl]aminomethyl}phenoxy)butyric acid of the following formula that is a selective PPARα-activating agent and is useful as a preventive and/or a therapeutic agent for hyperlipidemia, arteriosclerosis, diabetes, diabetes complications, inflammation, and cardiac disorders (Patent Document 1). In the manufacture of the above-described compound, optical purity of 2-hydroxybutyric acid serving as a synthesis intermediate, or a derivative thereof directly and considerably affects optical purity of the final product. Therefore, a pharmaceutical ingredient having higher optical purity is desired (Patent Documents 2 to 6).

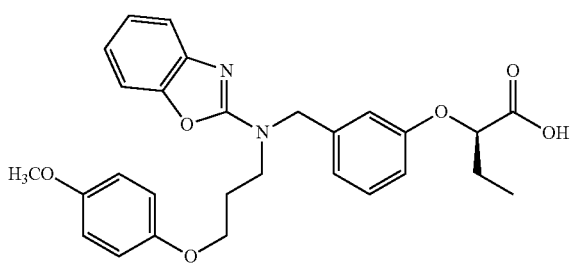 [SMILES: CC[C@@H](Oc1cccc(CN(CCCOc2ccc(OC)cc2)c2nc3ccccc3o2)c1)C(=O)O]

Such an optically active 2-hydroxybutyric acid derivative is, commercially available (Aldrich), but very expensive. Hitherto, there have been known several methods for manufacturing optically active 2-hydroxycarboxylic acid ester derivatives as shown in the following reaction schemes:
(1) Method for manufacturing an optically active 2-hydroxybutyric acid ester by asymmetric reduction of 2-keto butyric acid ester using a baker's yeast (Non-Patent Document 1),
(2) Method for manufacturing an optically active 2-hydroxybutyric acid ester using L-methionine as a starting material (Non-Patent Documents 2 and 3),
(3) Method for manufacturing an optically active 2-hydroxycarboxylic acid ester derivative by asymmetric reduction of an acrylic acid derivative (Non-Patent Document 4), and
(4) Method for manufacturing an optically active 2-hydroxycarboxylic acid derivative using an aldehyde as a starting material via optically active cyanohydrin (Patent Document 7).

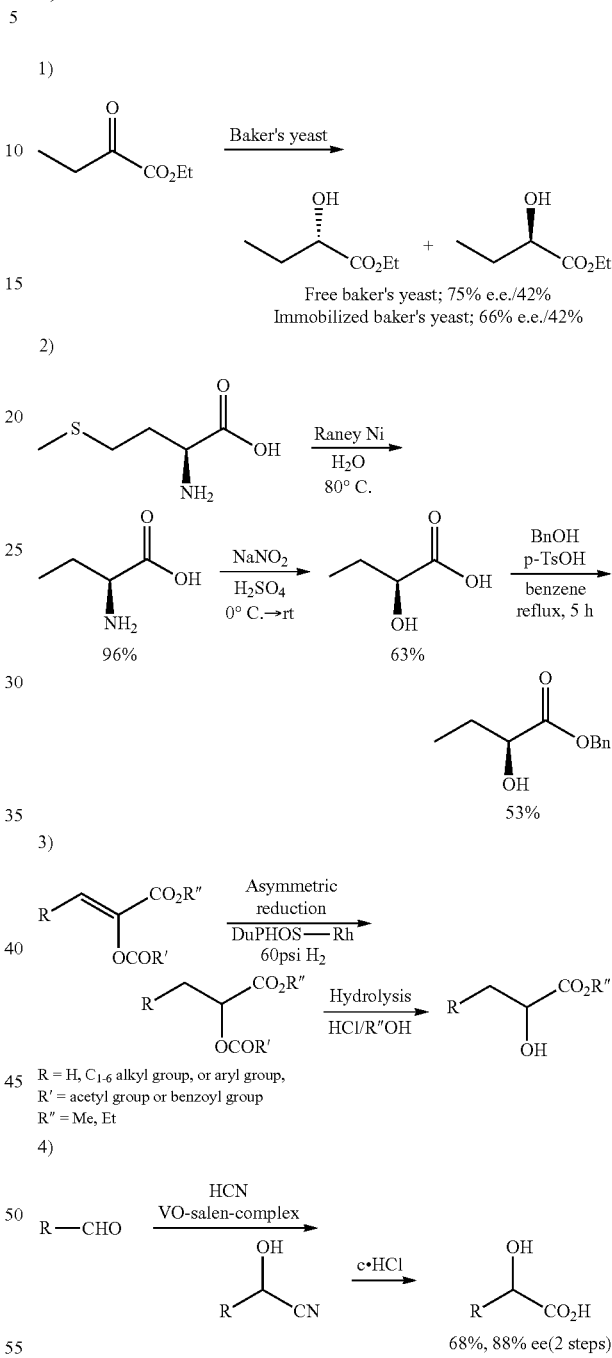

However, in method (1), the optical purity (S configuration) and the chemical yield of the resultant 2-hydroxybutyric acid ester are 75% e.e. and 42% respectively when free baker's yeast is used, and are 66% e.e. and 42% respectively when immobilized baker's yeast is used. Therefore, neither of them is suitable for manufacturing a 2-hydroxybutyric acid ester with high optical purity. Thus, method (1) is not an industrially available manufacturing method. In addition, a 2-keto butyric acid ester is chemically unstable and is expensive, which is problematic. Furthermore, optically active 2-hydroxycarboxylic acid ester having R configuration cannot be yielded through method (1).

In method (2), a target optically active 2-hydroxybutyric acid ester can be manufactured using inexpensive L-methionine as a starting material. However, three steps are required for the manufacture of the target product, and the total yield is as low as 32%. Furthermore, method (2) is not efficient, since, for example, a large amount of solvent is required for the reaction and post-treatment of reaction. Also, since the manufacturing method involves a step of forming an unstable diazonium salt, it is difficult to control the reaction conditions. As a result, consistent yield and optical purity of the target product may not be obtained, and the optical purity may be significantly lowered depending on the manufacturing scale.

In method (3), a target product having high optical purity can be yielded through asymmetrically reducing double bonds in a 2-acyloxyacrylic acid ester derivative through hydrolysis with acid in the presence of an asymmetric catalyst. However, cumbersome operations are required for producing a 2-acyloxyacrylic acid ester derivative serving as a starting substrate. In addition, method (3) is not an industrially advantageous manufacturing method, involving problems such as preparation of an expensive asymmetric ligand and carrying out reduction under high pressure hydrogen.

In method (4), a 2-hydroxy carboxylic acid derivative is manufactured in two steps, i.e., conversion of an aldehyde into asymmetric cyanohydrin and subsequent hydrolysis. This requires a cumbersome preparation of an asymmetric ligand serving as an asymmetric catalyst. With regard to optical purity, the optical purity and the chemical yield of the target are likely to vary depending on the substituent of the reaction substrate.

In a known alternative method, racemic 2-hydroxy butyric acid is transformed into a corresponding diastereomer salt by using brucine, and the salt is subjected to optical resolution (Non-Patent Document 5). The document does not disclose optical purity. Also reported is a kinetic optical resolution of 2-hydroxycarboxylic acid by using recombinant E. coli (Non-Patent Document 6). However, the method is not industrially practical.

Furthermore, it is reported the optical purity of an inorganic salt of 2-hydroxyhexanoic acid (Non-Patent Document 7). However, it is not known that a 2-hydroxycarboxylic acid having high optical purity and a derivative thereof can be produced from the thus-formed inorganic salt.

PRIOR ART DOCUMENTS

Patent Documents

Patent Document 1: WO 2005/23777
Patent Document 2: WO 2006/90768
Patent Document 3: WO 2006/93142
Patent Document 4: WO 2006/129649
Patent Document 5: WO 2007/13555
Patent Document 6: WO 2007/23906
Patent Document 7: Japanese PCT Kohyo Patent Application 2004-533490

Non-Patent Documents

Non-Patent Document 1: J. Org. Chem., 1988, 53, 2589-2593
Non-Patent Document 2: J. Org. Chem., 1986, 51, 1713-1719
Non-Patent Document 3: Chirality, 1996, 51, 225-233
Non-Patent Document 4: J. Am. Chem. Soc., 1988, 120, 4315-4353
Non-Patent Document 5: Nippon Kagaku Kaishi, 1956, 77, 2, 284
Non-Patent Document 6: Tetrahedron: Asymmetry, 2007, 18, 2394-2398
Non-Patent Document 7: J. Chem. Soc., 1954, 177, 1460-1464

SUMMARY OF THE INVENTION

Problems to be Solved by the Invention

An object of the present invention is to provide a method for improving optical purity of an optically active 2-hydroxycarboxylic acid or a derivative thereof, which is useful as a raw material in the manufacture of medicines, agrochemicals, and industrial products.

In view of the foregoing, the present inventor has conducted intensive studies to explore a method for improving optical purity of an optically active 2-hydroxycarboxylic acid or a derivative thereof. As a result, the present inventor has found that the optical purity of optically active 2-hydroxycarboxylic acid or derivative thereof can be improved by reacting an optically active 2-hydroxycarboxylic acid with at least one optically inactive base selected from the group consisting of an alkali metal alkoxide and a secondary amine, in the presence of a solvent, and recrystallizing the reaction product. The present invention has been accomplished on the basis of this finding. As used herein, the term "2-hydroxycarboxylic acid derivative" refers to a salt or an ester of a 2-hydroxycarboxylic acid.

Accordingly, the present invention is directed to the following.

(1) A method for improving optical purity of a hydroxycarboxylic acid of the following formula (1a) or (1b) or a derivative thereof, the method comprising the steps of:
reacting the hydroxycarboxylic acid of the following formula (1a) or (1b) with at least one optically inactive base selected from the group consisting of an alkali metal alkoxide and a secondary amine in the presence of a solvent, and, subsequently,
performing recrystallization, to thereby form a hydroxycarboxylic acid salt of the following formula (IIIa) or (IIIb).

(2) A method for improving optical purity of a hydroxycarboxylic acid of the following formula (1a) or (1b) or a derivative thereof, the method comprising:
a first step of reacting the hydroxycarboxylic acid of the following formula (1a) or (1b) with at least one optically inactive base selected from the group consisting of an alkali metal alkoxide and a secondary amine in the presence of a solvent and, subsequently, performing recrystallization, to thereby form a hydroxycarboxylic acid salt of the following formula (IIIa) or (IIIb), and a second step of reacting the hydroxycarboxylic acid salt with an organic acid or an inorganic acid, to thereby form the hydroxycarboxylic acid of formula (1a) or (1b).

(3) A method for improving optical purity of a hydroxycarboxylic acid of the following formula (1a) or (1b) or a derivative thereof, the method comprising:

a first step of reacting the hydroxycarboxylic acid of the following formula (1a) or (1b) with at least one optically inactive base selected from the group consisting of an alkali metal alkoxide and a secondary amine in the presence of a solvent and, subsequently, performing recrystallization, to thereby form a hydroxycarboxylic acid salt of the following formula (IIIa) or (IIIb), a second step of reacting the hydroxycarboxylic acid salt with an organic acid or an inorganic salt, to thereby form the hydroxycarboxylic acid of formula (1a) or (1b), and a third step of esterifying the hydroxycarboxylic acid formed in the second step.

(4) A method for improving optical purity of a hydroxycarboxylic acid of the following formula (1a) or (1b) or a derivative thereof, the method comprising the steps of:

reacting the hydroxycarboxylic acid of the following formula (1a) or (1b) with at least one optically inactive base selected from the group consisting of an alkali metal alkoxide and a secondary amine in the presence of a solvent and, subsequently, performing recrystallization, to thereby form a hydroxycarboxylic acid salt of the following formula (IIIa) or (IIIb), and esterifying the hydroxycarboxylic acid salt.

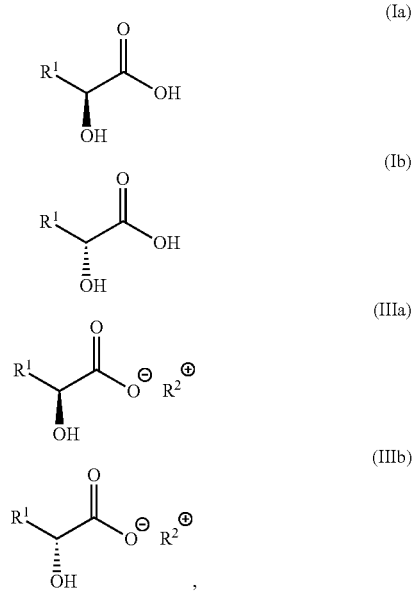

wherein $R^1$ represents a $C_{1-8}$ alkyl group, and $R^2$ represents an alkali metal or a secondary amine.

(5) More specifically, the method as described in any one of (1) to (4) above, wherein $R^1$ is an ethyl group.

(6) More specifically, the method as described in any one of (1) to (5) above, wherein the optically inactive base is a sodium alkoxide.

(7) The method as described in (6) above, wherein the sodium alkoxide is sodium methoxide.

(8) The method as described in any one of (1) to (7) above, wherein the optically inactive base is dicyclohexylamine.

(9) The method as described in any one of (1) to (8) above, wherein recrystallization is performed by using a solvent containing at least one solvent selected from the group consisting of an ester, an ether and an alcohol.

(10) A method for producing a compound of the following formula (A), the method comprising a method as recited in any one of (1) to (9) above.

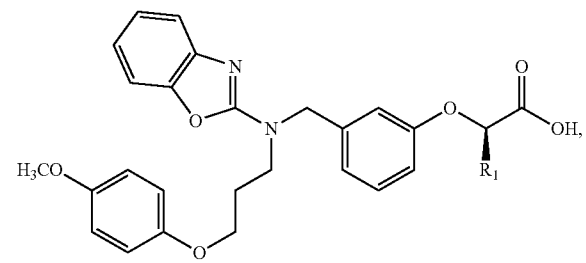

wherein $R^1$ represents a $C_{1-8}$ alkyl group.

(11) The method as described in (10) above, wherein the formula (A) is (R)-2-(3-{N-(benzoxazol-2-yl)-N-[3-(4-methoxyphenoxy)propyl]aminomethyl}phenoxy)butyric acid.

Effects of the Invention

According to the method of the present invention, the optical purity of an optically active 2-hydroxycarboxylic acid or a derivative thereof that are useful as raw materials in the manufacture of medicines, agrochemicals, and industrial products can be improved.

MODES FOR CARRYING OUT THE INVENTION

The compound of the present invention of the above-described formula (1a) or (1b), hereinafter also referred to as "carboxylic acid (1a) or (1b)", can be produced in accordance with the following scheme 1. The compound of the following formula (IIIa) or (IIIb), hereinafter also referred to as "a carboxylic acid salt (IIIa) or (IIIb)", can be produced by reacting the carboxylic acid (1a) or (1b) of the present invention with a optically inactive base. The compound of the following formula (IVa) or (IVb), hereinafter also referred to as "ester (IVa) or (IVb)", can be produced by esterifying the carboxylic acid (1a) or (1b) of the present invention. These compounds can serve as an intermediate of synthesis of pharmaceutically useful compounds. In production of the carboxylic acid (1a) or (1b), the compound of the following formula (IIa) or (IIb), hereinafter also referred to as "amino acid (IIa) or (IIb)", may be used as a raw material. The method for producing the carboxylic acid (1a) or (1b) is not limited to these methods, and the carboxylic acid (1a) or (1b) may be produced through any known method.

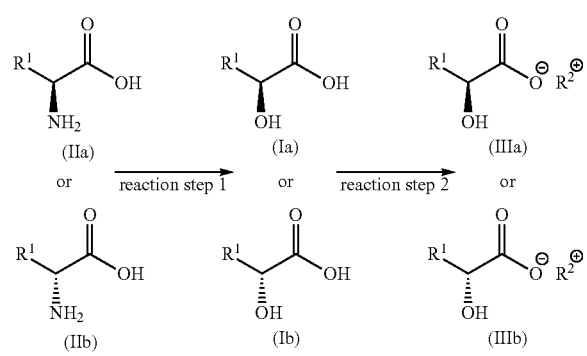

-continued

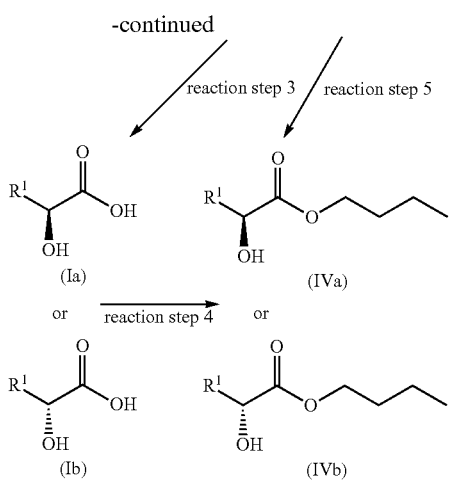

wherein $R^1$ represents $C_{1-9}$ alkyl group, and $R^2$ represents an alkali metal or a secondary amine.

As the $C_{1-8}$ alkyl group of $R^1$, a $C_{1-6}$ alkyl group is preferable, and a $C_{1-3}$ alkyl group is more preferable. The alkyl group may be linear or branched, and linear form is preferable. Specific examples include a methyl group, an ethyl group, an n-propyl group, an isopropyl group, and the like. Among them, an ethyl group is preferable.

Hereinafter, each reaction step is described based on scheme 1.

[Reaction Step 1]

This step is for converting an amino group in the amino acid (IIa) or (IIb) into a hydroxyl group with stereoretention of the amino group, to thereby produce the carboxylic acid (1a) or (1b).

The reagents, the solvents and the reaction conditions employed in reaction step 1 are not specifically limited. For example, the method described in "Chirality, 1996, 51, 225-233" or "Tetrahedron, 1976, 32, 1101-1106" may be employed. There may be also employed hydroxylation via diazotization of amine with a diazotization reagent in the presence or absence of a solvent. No particular limitation is imposed on the diazotization reagent, and examples thereof include sodium nitrite, nitrous acid, and the like.

If necessary, the carboxylic acid (1a) or (1b) yielded in step 1 may be isolated and/or purified through a purification method generally employed in synthetic organic chemistry, such as filtration, extraction, washing, drying, concentration, recrystallization, and a variety of chromatography techniques. Alternatively, the carboxylic acid may be used in the subsequent step without any further purification.

[Reaction Step 2]

In reaction step 2, the carboxylic acid (1a) or (1b) is reacted with at least one optically inactive base selected from the group consisting of an alkali metal alkoxide and a secondary amine in the presence of a solvent, and then performing recrystallization, to thereby form a carboxylic acid salt (IIIa) or (IIIb), having an improved optical purity.

The alkali metal alkoxide and the secondary amine may be used singly or in combination of two or more species. Also, the alkali metal alkoxide may be used in combination with the secondary amine.

No particular limitation is imposed on the alkali metal alkoxide, so long as it is optically inactive. A commercially available alkali metal alkoxide as is may be used. Alternatively, an alkali metal, an alkali metal hydride, or an alkali metal amide is reacted with alcohol, and the reaction product may be used as the alkali metal alkoxide. Examples of the alkali metal alkoxide include $C_{1-6}$ alkoxides of lithium, potassium, sodium, and the like. The $C_{1-6}$ alkoxide may be any of linear, branched, and cyclic. Specific examples include sodium alkoxides such as sodium methoxide, sodium ethoxide, sodium tert-butoxide, and sodium phenoxide; and potassium alkoxides such as potassium methoxide, potassium ethoxide, potassium tert-butoxide, and potassium phenoxide. Among them, sodium alkoxides are preferable, and sodium methoxide is more preferable.

No particular limitation is imposed on the secondary amine, but a dialkyl amine is preferable. A variety of dialkyl amines that have the same kind of alkyl groups or a different kind of alkyl groups may be used. The alkyl group may be linear, branched, and cyclic, so long as it is optically inactive, and a cyclic alkyl group is preferable. As the dialkyl amine, a di($C_{1-8}$ alkyl)amine is preferable, a di($C_{3-6}$ alkyl)amine is more preferable, and di($C_{3-6}$ cyclic alkyl)amine is still more preferable. Specific examples include dimethylamine, diethylamine, dipropylamine, diisopropylamine, dicylohexylamine, N-ethylmethylamine, N-methylpropylamine, N-isopropylmethylamine, N-methylcyclohexylamine, N-ethylpropylamine, N-ethylisopropylamine, N-ethylcyclohexylamine, N-propylisopropylamine, N-propylcyclohexylamine, N-isopropylcyclohexylamine, and the like. Among these, dicyclohexylamine is preferable.

No particular limitation is imposed on the amount of the optically inactive base used in the invention, so long as a salt of the carboxylic acid (1a) or (1b) with the base (1:1 by mole) can be formed and precipitated as crystals. From the standpoint of further improving the optical purity, from 0.7 to 1.5 mol eq. to the carboxylic acid (1a) or (1b) is preferable, and from 90.9 to 1.2 mol eq. is more preferable.

No particular limitation is imposed on the solvent used in the reaction with the optically inactive base, so long as it can dissolve the carboxylic acid (1a) or (1b). Examples of the solvent include alcohols such as methanol, ethanol, and isopropanol; and ethers such as tetrahydrofuran, diethyl ether, dioxane, methyl tert-butyl ether (MTBE), and cyclopentyl methyl ether. Among them, ethers are preferable. These solvents may be used singly or in combination of two or more species. In addition, the below-mentioned solvent used for recrystallization may also be employed here. The amount of the solvent is appropriately tuned, and preferably from 10 to 50 (v/w) times as much as the weight of the carboxylic acid (1a) or (1b), and more preferably from 15 to 35 (v/w) times as much. As used herein, "v/w" means a volume/weight ratio on L/kg basis.

The reaction temperature may be appropriately selected depending on the types of the optically inactive base to be employed, and is preferably from −20° C. to 100° C., and more preferably from −10° C. to 80° C. The reaction time is preferably from 10 to 300 minutes, and more preferably from 20 to 120 minutes.

After the reaction is terminated, the salt precipitated from the reaction mixture may be collected through filtration, and optionally subsequent washing and solvent evaporation, to form the carboxylic acid salt (IIIa) or (IIIb). In the present invention, the carboxylic acid salt (IIIa) or (IIIb) can be employed in the subsequent recrystallization as described hereafter, without isolating the carboxylic acid salt (IIIa) or (IIIb). Examples of the recrystallization method include the following:

i) A method in which the carboxylic acid (1a) or (1b) and an optically inactive base are dissolved in a solvent, followed by subjecting them to a reaction and optional cooling; and ii) A method in which the carboxylic acid salt (IIIa) or (IIIb) is heated and dissolved in a solvent, optionally with addition of a poor solvent or solvent substitution with a poor solvent, and/or optionally followed by cooling.

No particular limitation is imposed on the solvent used in the recrystallization. Examples of the solvent include halogenated hydrocarbons such as dichloromethane and chloroform; ethers such as tetrahydrofuran, diethyl ether, dioxane, methyl tert-butyl ether (MTEB), and cyclopentylmethyl ether; aromatic hydrocarbons such as benzene, toluene, and xylene; alcohols such as methanol, ethanol, and isopropanol; esters such as ethyl acetate and isopropyl acetate; nitriles such as acetonitrile and propionitrile; aprotic polar solvents such as dimethylformamide and dimethyl sulfoxide; and hydrocarbons such as n-hexane and n-heptane. Among them, the solvent preferably contains at least one member selected from the group consisting of an ester, an ether, and an alcohol, and more preferably contains at least one member selected from the group consisting of methyl tert-butyl ether, cyclopentylmethyl ether, methanol, ethanol, isopropanol, ethyl acetate, and propyl acetate. These solvents may be used singly or in combination of two or more. When solvents are used in combination, although not limiting, a preferable combination is alcohol/hydrocarbon and alcohol/ester, and a more preferable combination is isopropanol/n-heptane, ethanol/n-heptane, or methanol/methyl tert-butyl ether. When the carboxylic acid salt is an alkali metal salt, the amount ratio (v/v) is preferably from 1/8 to 4/1, more preferably from 1/4 to 2/1. When the carboxylic acid salt is an amine salt, the amount ratio (v/v) is preferably from 1/2 to 1/12, and more preferably from 1/5 to 1/10.

The amount of the solvent used for recrystallization is preferably from 3 to 65 (v/w) times as much as the weight of the carboxylic acid salt (IIIa) or (IIIb), and more preferably from 10 to 15 (v/w) times as much.

No particular limitation is imposed on the temperature at which the compound is dissolved upon recrystallization, and the temperature is preferably, for example, from 20° C. to 100° C., more preferably from 50° C. to 80° C. The cooling temperature is preferably, for example, from 20 to 30° C. If necessary, the cooling may be performed under stirring.

[Reaction Step 3]

In reaction step 3, the carboxylic acid salt (IIIa) or (IIIb) having an improved optical purity is reacted with an organic acid or an inorganic acid, to thereby produce the carboxylic acid (1a) or (1b) having an improved optical purity.

This step can be performed in a solvent. No particular limitation is imposed on the solvent, so long as it can dissolve the carboxylic acid salt (IIIa) or (IIIb). Examples of the solvent include alcohols such as methanol, ethanol, isopropanol, and n-butanol; aromatic hydrocarbon such as benzene, toluene, and xylene; ethers such as tetrahydrofuran, diethyl ether, dioxane, methyl tert-butyl ether (MTBE), and cyclopentylmethyl ether; esters such as ethyl acetate and isopropyl acetate; nitriles such as acetonitrile and propionitrile; hydrocarbons such as n-hexane and n-heptane; and water. These solvents may be used singly or in combination of two or more species. The amount of the solvent used in the invention may be tuned depending on the solubility of the carboxylic acid salt (IIIa) or (IIIb), as appropriate. The amount of the solvent is preferably from 1 to 20 (v/w) times as much as the weight of the carboxylic acid salt (IIIa) or (IIIb), and more preferably from 1 to 10 (v/w) times as much.

Non-limiting examples of the inorganic acid include hydrochloric acid, hydrobromic acid, hydriodic acid, sulfuric acid, nitric acid, and phosphoric acid. Non-limiting examples of the organic acid include methanesulfonic acid, ethanesulfonic acid, and p-toluenesulfonic acid. The amount of the acid to be employed is preferably from 1 to 5 mol eq. to the carboxylic acid salt (IIIa) or (IIIb), and more preferably from 1 to 2 mol eq.

The reaction temperature is preferably from −20° C. to 80° C., and more preferably from 0° C. to 40° C. The reaction time is preferably from 0.1 to 12 hours, and more preferably from 0.1 to 2 hours.

After the reaction, if necessary, a solvent and water are added to the reaction mixture for phase separation, and the organic layer is concentrated, thereby providing the carboxylic acid (1a) or (1b) having an improved optical purity. The aforementioned solvents may also be employed. According to the present invention, the carboxylic acid (1a) or (1b) may be employed in a subsequent step, without isolating the carboxylic acid (1a) or (1b).

[Reaction Step 4]

In reaction step 4, an ester (IVa) or (IVb) is produced by condensing the carboxylic acid (1a) or (1b) having an improved optical purity with a monovalent aliphatic alcohol by using a condensation agent in a solvent in the presence or absence of a condensation accelerator. Alternatively, the ester (IVa) or (IVb) may be produced by reacting the carboxylic acid (1a) or (1b) with a monovalent aliphatic alcohol in a solvent in the presence of an acid catalyst, which is a common technique for producing an ester. Still alternatively, the ester (IVa) or (IVb) may be produced by converting the carboxylic acid (1a) or (1b) into a reactive derivative in a solvent and reacting the derivative with a monovalent aliphatic alcohol, which is a common method for producing an ester. The monovalent aliphatic alcohol is preferably a $C_{1-8}$ aliphatic monoalcohol, more preferably a $C_{1-6}$ aliphatic monoalcohol, and may have a linear chain or branched chain. Specific examples include methanol, ethanol, n-propanol, n-butanol, and the like. Among them, n-butanol is preferable. Scheme 1 shows a specific example in which n-butanol is used as the aliphatic alcohol in the esterification reaction.

Non-limiting examples of the solvent include halogen hydrocarbons such as 1,2-dichloroethane, chloroform, and dichloromethane; esters such as ethyl acetate and isopropyl acetate; aromatic hydrocarbons such as toluene and benzene; ethers such as tetrahydrofuran and 1,4-dioxane; nitriles such as acetonitrile and propionitrile; amides such as N,N-dimethylformamide and N-methylpyrrolidone; and water. These solvents may be used singly or in combination of two or more species.

Non-limiting examples of the condensation accelerator include DMAP, HOAt, HOBt, HODhbt, HONB, HOPfp, HOPht, HOSu, and the like. Non-limiting examples of the condensation agent include DCC, DIPCI, WSCI, WSC.HCl, DEPC, BOP, PyBOP, TBTU, and the like.

Non-limiting examples of the acid include inorganic acids such as hydrochloric acid, hydrobromic acid, hydriodic acid, sulfuric acid, nitric acid, and phosphoric acid; and organic acids such as methane sulfonate, ethane sulfonate, and p-toluene sulfonate. Non-limiting examples of the reactive derivative include an acid halide, a mixed acid anhydride with pivalic acid; and a p-nitrophenyl ester. The reaction temperature is from −20° C. to 150° C., and more preferably from 80° C. to 130° C. The reaction time is preferably from 5 minutes to 24 hours, and more preferably from 10 minutes to 12 hours.

[Reaction Step 5]

In reaction step 5, the ester (IVa) or (IVb) is produced by reacting the carboxylic acid salt (IIIa) or (IIIb) having an improved optical purity with a monovalent aliphatic alcohol in a solvent in the presence of an acid catalyst, or with a monovalent halogenated aliphatic hydrocarbon under basic conditions. The monovalent halogenated aliphatic hydrocarbon is preferably a $C_{1-8}$ alkyl halide, more preferably a $C_{1-6}$ alkyl halide, and the alkyl group may have a linear chain or branched chain. Examples of the halogen include fluorine, chlorine, bromine, and iodine. Specific examples of the monovalent halogenated aliphatic hydrocarbon include methyl bromide, ethyl chloride, isopropyl chloride, n-butyl chloride, and the like. Examples of the monovalent aliphatic alcohol include those as described above, and preferable embodiments are as described above, too. Scheme 1 shows specific example in which n-butyl chloride and n-butanol are in the esterification reaction.

As the solvent and the acid catalyst used in the esterification, those commonly used in esterification may be used without limitation. For example, solvents and acid catalysts similar to those employed in the above-described reaction processes 3 and 4 may be used. Examples of the base catalyst include sodium hydroxide and potassium hydroxide. The amount of the solvent used in the invention, the acid catalyst and the base catalyst, the reaction temperature, and the reaction time may be the same as employed in the above-described reaction steps 3 and 4.

Note that the compound of formula (A) (for example, (R)-2-(3-{N-(benzoxazol-2-yl)-N-[3-(4-methoxyphenoxy)propyl]aminomethyl}phenoxy)butyric acid) is produced by the method described in, for example, WO 2005/23777, WO 2006/90768, and WO 2006/93142, by using 2-hydroxycarboxylic acid of formula (1a) or (1b) or a derivative thereof in the above-described reaction step. In one embodiment, a hydroxyl group in the ester (IVa) or (IVb) formed in the above-described reaction step is transformed into a trifluoromethanesulfonylozy group, which is reacted with the compound of the following formula (B) in the presence of a base, to thereby form a corresponding phenyl ether. Then, the compound is de-esterified. The entire content of all patent documents and non-patent documents cited in the present specification is incorporated by reference herein.

[F6]

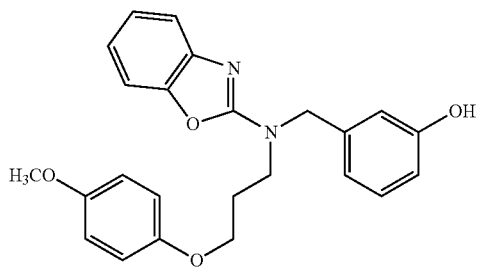

(B)

The ester (IVa) or (IVb) formed in reaction steps 4 and 5 may be isolated and purified by a purification technique commonly employed in organic synthetic chemistry such as filtration, extraction, washing, drying, concentration, recrystallization, or a variety of chromatography techniques, if required.

Isomers of the target compound can be isolated through applying a conventional method employing difference in physical and chemical properties between the isomers. A racemic mixture can be transformed into an optically pure isomer through a conventional optical resolution technique such as optical resolution of a diastezeomer salt with a general optically active acid such as tartaric acid; or through optically active column chromatography. Also, a diastereomer mixture can be separated through fractionated crystallization or a variety of chromatography techniques. Alternatively, an optically active compound may be produced by using an appropriate optically active raw material.

EXAMPLES

The present invention will next be described in detail by way of examples, which should not be construed as limiting the invention thereto. The symbols used in the following Examples have the following meanings.
s: singlet
d: doublet
t: triplet
m: multiplet
J: coupling constant
Hz: Hertz
$CDCl_3$: Deuterated chloroform
e.e.: enantiomeric excess
GC: gas chromatography
MTBE: methyl tert-butyl ether
DCHA: dicyclohexylamine Production Example 1

Method of synthesizing (S)-2-hydroxybutyric acid (S)-2-Aminobutyric acid (20.0 g, 194 mmol) was dissolved in 1N sulfuric acid (228 mL). At −5° C., an aqueous solution of sodium nitrite (26.8 g, 338 mmol) (68 mL) was added dropwise thereinto, and stirred for 0.5 hours. The mixture was further stirred for 2 hours at room temperature. The reaction mixture was cooled to 0° C., and sulfuric acid was added such that the pH of the reaction mixture became 1. The resultant mixture was stirred for 12 hours at room temperature. To the reaction mixture, sodium chloride (120 g) and MTBE (120 mL) were added, and the mixture was stirred for 30 minutes and subjected to extraction with MTBE. The organic layer was washed with saturated saline, dried over anhydrous sodium sulfate, and concentrated under reduced pressure, thereby providing the title compound (13.8 g, 69%) as a pale yellow solid.
$^1$H NMR (400 MHz, $CDCl_3$) δ 1.00 (t, J=7.6 Hz, 3H), 1.68-1.79 (m, 1H), 1.84-1.93 (m, 1H), 4.24 (dd, J=6.8, 4.4 Hz, 1H).

Example 1

1. Synthesis of Dicyclohexylamine (DCHA) Salt
(S)-2-Hydroxybutyric acid (6.44 g) was dissolved in MTBE (200 mL). Under stirring, DCHA (12.3 g, 1.1 eq.) was added dropwise thereinto. After stirring at 25° C. for 1.5 hours, the solid was recovered through filtration and washed with MTBE (30 mL×3). The resultant solid was dried at 70° C. under reduced pressure up to a constant mass, thereby yielding a colorless solid (16.2 g, 92%).
2. Synthesis of Sodium (Na) Salt
(S)-2-Hydroxybutyric acid (4.00 g) was dissolved in MeOH (60 mL). While the solution was stirred under ice cooling, MeONa (38.4 g, 1.0 eq.) was added. After stirring for 30 minutes, the reaction mixture was concentrated under reduced pressure, to thereby form a colorless solid. The resultant solid was suspended in and washed with MTBE (in appropriate amount), and the solid was recovered through filtration and washed with MTBE (appropriate amount). The resultant solid was dried at room temperature under reduced pressure up to a constant mass, thereby yielding a colorless solid (4.29 g, 89%).

3. Recrystallization

The DCHA salt (A) or Na salt (B) were heated and dissolved in a solvent, and the solution was returned to room temperature under stirring. After overnight stirring, crystals were recovered through filtration and washed with the solvent used (A; 2 mL×3, B; 1 mL). The resultant crystals were dried at 25° C. under reduced pressure up to a constant mass (See Table 1. In entries 4, 6 to 9, crystals were dissolved in alcohol, and a poor solvent was added).

4. Determination of Optical Purity

To a (S)-2-hydroxybutyric acid salt (1.75 mmol) formed through the recrystaillization, n-BuOH (1 mL) containing sulfuric acid (50 µL) was added, and the mixture was stirred for 6 hours at 110° C. The mixture was brought back to room temperature, and 0.5N HCl (6 mL) and AcOEt (3 mL) were added, followed by sufficient mixing. The organic layer (2 mL) was dried over sodium sulfate. Thereafter, the supernatant was filtered over a Millipore filter. An aliquot (1 mL) thereof was used as a sample for GC measurement, and was diluted with a solvent as appropriate, whereby the optical purity of the sample was measured. The conditions for the GC measurement are as follows.

Measurement Conditions
Detector: hydrogen flame ionization detector
Column: InertCap CHIRAMIX manufactured by GL Sciences
Column temperature: injected at a constant temperature around 100° C. and held for 20 minutes. Thereafter, the temperature elevated to 140° C. by 2° C. per minute.
Inlet temperature: 230° C.
Detector temperature: 250° C.
Carrier gas: helium
Flowrate: 1.0 mL/min
Split ratio: 20:1

The relative retention time of (S)-2-hydroxybutyric acid is 0.96 minutes.

TABLE 1

| Entry | Type of salt* | Solvent | Solvent amount | Dissolution temperature | Yield | Optical purity |
|---|---|---|---|---|---|---|
| 1 | A. 1.0 g | ethyl acetate | 30 mL | 80° C. | 911 mg | 98.9% e.e. |
| 2 | A. 1.0 g | isopropyl acetate | 30 mL | 80° C. | 901 mg | 98.3% e.e. |
| 3 | A. 1.0 g | methyl cyclopentyl ether | 20 mL | 80° C. | 852 mg | 98.8% e.e. |
| 4 | A. 1.0 g | IPA/ n-heptane (1/8) | 45 mL | 80° C. | 724 mg | 99.6% e.e. |
| 5 | B. 1.0 g | ethanol | 20 mL | 80° C. | 537 mg | 99.7% e.e. |
| 6 | B. 0.5 g | ethanol/ n-heptane (3/2) | 25 mL | 70° C. | 328 mg | 99.7% e.e. |
| 7 | B. 0.5 g | ethanol/ n-heptane (1/1) | 30 mL | 70° C. | 348 mg | 99.6% e.e. |
| 8 | B. 1.0 g | methanol/ MTBE (1/1) | 12 mL | 50° C. | 319 mg | 99.9% e.e. |
| 9 | B. 0.5 g | methanol/ MTBE (1/2) | 9 mL | 50° C. | 332 mg | 99.3% e.e. |

*A: dicyclohexylamine salt (97.6% e.e.), B: sodium salt (96.5% e.e.).

Example 2

Synthesis of (S)-butyl 2-hydroxybutanoate

To a suspension of sodium (S)-2-hydroxybutyrate (18.0 g, 0.14 mol, 93.4%, e.e.) obtained by the same process as employed in Example 1 in n-butanol (140 mL), n-butanol (40 mL) containing sulfuric acid (11.2 g, 0.11 mol) was slowly added at room temperature. The resultant mixture was heated to 110° C., stirred for 1.5 hours, and ice-cooled to 0° C. A 10% aqueous solution of potassium bicarbonate (180 mL) was slowly added thereto at 2.0 to 14.5° C., and the mixture was stirred for 0.5 hours. The resultant organic layer was washed with saturated saline, dried over anhydrous sodium sulfate, and concentrated under reduced pressure, to thereby provide colorless oil (17.5 g, 79%, 98.9% e.e.).

INDUSTRIAL APPLICABILITY

The present invention provides a method for improving optical purity of 2-hydroxycarboxylic acid of the above-described formula (1a) or (1b) or a derivative thereof. The present invention enables production of an important raw material of (R)-2-(3-{N-(benzoxazol-2-yl)-N-[3-(4-methoxyphenoxy)propyl]aminomethyl}phenoxy)butyric acid of formula (A), which is useful as a preventive and/or a therapeutic agent for hyperlipidemia, arteriosclerosis, diabetes, diabetes complications, inflammation, and cardiac disorders. Thus, the present invention has industrial applicability. The compound of formula (A) (for example, (R)-2-(3-{N-(benzoxazol-2-yl)-N-[3-(4-methoxyphenoxy)propyl]aminomethyl}phenoxy) butyric acid) can be manufactured by using 2-hydroxycarboxylic acid of the above-described formula (1a) or (1b) or a derivative thereof through a method described in WO 2005/23777, WO 2006/90768, WO 2006/93142, or the like.

The invention claimed is:

1. A method for improving optical purity of a hydroxycarboxylic acid of the following formula (1a) or (1b) or a derivative thereof, the method comprising the steps of:
   reacting the hydroxycarboxylic acid of the following formula (1a) or (1b):

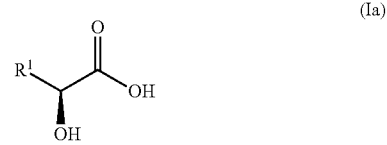

(Ia)

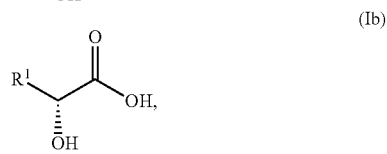

(Ib)

wherein $R^1$ represents a $C_{1-8}$ alkyl group, with at least one optically inactive base selected from the group consisting of an alkali metal alkoxide and a secondary amine in the presence of a solvent and, subsequently,
   performing recrystallization, to thereby form a hydroxycarboxylic acid salt of the following formula (IIIa) or (IIIb):

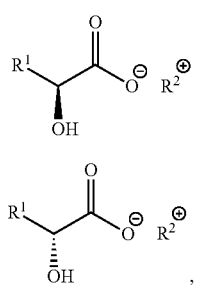

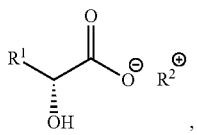

wherein $R^1$ has the same meaning as defined above, and $R^2$ represents an alkali metal or a secondary amine.

2. A method for improving optical purity of a hydroxycarboxylic acid of the following formula (1a) or (1 b) or a derivative thereof, the method comprising a first step of:

reacting the hydroxycarboxylic acid of the following formula (1a) or (1 b):

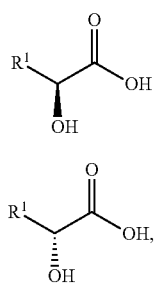

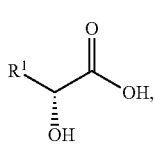

wherein $R^1$ represents a $C_{1-8}$ alkyl group, with at least one optically inactive base selected from the group consisting of an alkali metal alkoxide and a secondary amine in the presence of a solvent and, subsequently, performing recrystallization, to thereby form a hydroxycarboxylic acid salt of the following formula (IIIa) or (IIIb):

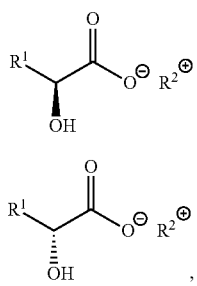

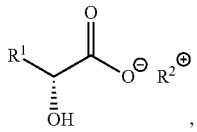

wherein $R^1$ has the same meaning as defined above, and $R^2$ represents an alkali metal or a secondary amine, and a second step of:

reading the hydroxycarboxylic acid salt with an organic acid or an inorganic acid, to thereby form the hydroxycarboxylic acid of formula (1a) or (1b).

3. A method for improving optical purity of a hydroxycarboxylic acid of the following formula (1a) or (1 b) or a derivative thereof, the method comprising a first step of:

reacting the hydroxycarboxylic acid of the following formula (1a) or (1 b):

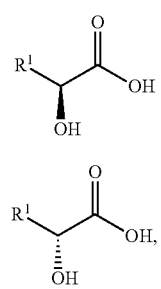

wherein $R^1$ represents a $C_{1-8}$ alkyl group, with at least one optically inactive base selected from the group consisting of an alkali metal alkoxide and a secondary amine in the presence of a solvent and, subsequently, performing recrystallization, to thereby form a hydroxycarboxylic acid salt of the following formula (IIIa) or (IIIb):

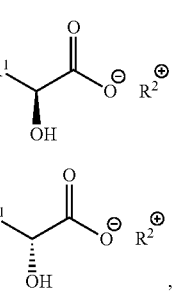

wherein $R^1$ has the same meaning as defined above, and $R^2$ represents an alkali metal or a secondary amine, a second step of reacting the hydroxycarboxylic acid salt with an organic acid or an inorganic acid to thereby obtain a hydroxycarboxylic acid of the following formula (1a) or (1b), and a step of esterifying the hydroxycarboxylic acid formed in the second step.

4. A method for improving optical purity of a hydroxycarboxylic acid of the following formula (1a) or (1 b) or a derivative thereof, the method comprising the steps of:

reacting the hydroxycarboxylic acid of the following formula (1a) or (1 b):

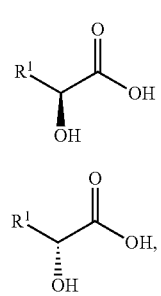

wherein $R^1$ represents a $C_{1-8}$ alkyl group, with at least one optically inactive base selected from the group consisting of alkali metal alkoxide and secondary amine in the presence of a solvent and, subsequently, performing recrystallization, to thereby form a hydroxycarboxylic acid salt of the following formula (IIIa) or (IIIb):

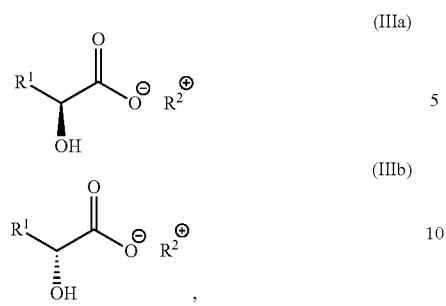

(IIIa)

(IIIb)

wherein R¹ has the same meaning as defined above, and R² represents an alkali metal or a secondary amine, and esterifying the hydroxycarboxylic acid salt.

5. A method according to any one of claims 1 to 4, wherein R¹ is an ethyl group.

6. A method according to any one of claims 1 to 4, wherein the optically inactive base is a sodium alkoxide.

7. A method according to claim 6, wherein the sodium alkoxide is sodium methoxide.

8. A method according to any one of claims 1 to 4, wherein the optically inactive base is dicyclohexylamine.

9. A method according to any one of claims 1 to 4, wherein recrystallization is performed using a solvent containing at least one member selected from the group consisting of an ester, an ether, and an alcohol.

* * * * *

UNITED STATES PATENT AND TRADEMARK OFFICE
CERTIFICATE OF CORRECTION

PATENT NO.       : 9,682,913 B2
APPLICATION NO.  : 14/780625
DATED            : June 20, 2017
INVENTOR(S)      : Yukiyoshi Yamazaki It is certified that error appears in the above-identified patent and that said Letters Patent is hereby corrected as shown below:

On the Title Page

Item (57), Line 10, "an alkali metal, alkoxide" should read --an alkali metal alkoxide--.

In the Claims

Claim 2, Column 15, Line 18, "formula (1 a) or (1 b)" should read --formula (1a) or (1b)--;

Claim 2, Column 15, Line 21, "formula (1a) or (1 b)" should read --formula (1a) or (1b)--;

Claim 2, Column 15, Line 60, "reading the hydroxycarboxylic acid salt" should read --reacting the hydroxycarboxylic acid salt--;

Claim 3, Column 15, Line 64, "formula (1a) or (1 b)" should read --formula (1a) or (1b)--;

Claim 3, Column 16, Line 67, "formula (1a) or (1 b)" should read --formula (1a) or (1b)--;

Claim 4, Column 16, Line 44, "formula (1a) or (1 b)" should read --formula (1a) or (1b)--;

Claim 4, Column 16, Line 47, "formula (1a) or (1 b)" should read --formula (1a) or (1b)--.

Signed and Sealed this
Twenty-sixth Day of September, 2017

Joseph Matal
*Performing the Functions and Duties of the
Under Secretary of Commerce for Intellectual Property and
Director of the United States Patent and Trademark Office*